(12) United States Patent
Drobnik et al.

(10) Patent No.: US 6,969,344 B2
(45) Date of Patent: Nov. 29, 2005

(54) END PORTION OF FIRST IMPLANTATION SEED SPACER THAT RECEIVES AND HOLDS ANY ONE OF IMPLANTATION SEED AND SECOND IMPLANTATION SEED SPACER

(75) Inventors: Christopher D. Drobnik, Wauconda, IL (US); Michael W. Drobnik, Downers Grove, IL (US); Scott C. Jones, Bloomingdale, IL (US)

(73) Assignee: Bard Brachytherapy, Inc., Carol Stream, IL (US)

( * ) Notice: Subject to any disclaimer, the term of this patent is extended or adjusted under 35 U.S.C. 154(b) by 0 days.

(21) Appl. No.: 10/361,530

(22) Filed: Feb. 10, 2003

(65) Prior Publication Data

US 2004/0158117 A1    Aug. 12, 2004

(51) Int. Cl.[7] .................................................. A61N 5/00
(52) U.S. Cl. ........................................................ 600/3
(58) Field of Search ........................................ 600/1–8

(56) References Cited

U.S. PATENT DOCUMENTS

| | | |
|---|---|---|
| 2,153,889 A | 4/1939 | Hames |
| 4,509,506 A | 4/1985 | Windorski et al. |
| 4,697,575 A | 10/1987 | Horowitz |
| 4,754,745 A | 7/1988 | Horowitz |
| 4,763,642 A | 8/1988 | Horowitz |
| 4,784,116 A | 11/1988 | Russell, Jr. et al. |
| 4,815,449 A | 3/1989 | Horowitz |
| 5,713,828 A | 2/1998 | Coniglione |
| 5,738,663 A | 4/1998 | Lopez |
| 6,010,446 A | 1/2000 | Grimm |
| 6,060,036 A | 5/2000 | Armini |
| 6,080,099 A | 6/2000 | Slater et al. |
| 6,163,947 A | 12/2000 | Coniglione |
| 6,200,258 B1 | 3/2001 | Slater et al. |
| 6,221,003 B1 * | 4/2001 | Sierocuk et al. ............... 600/7 |
| 6,264,599 B1 | 7/2001 | Slater et al. |
| 6,264,600 B1 | 7/2001 | Grimm |
| 6,273,851 B1 | 8/2001 | Slater et al. |
| 6,283,911 B1 * | 9/2001 | Keren .......................... 600/3 |
| 6,450,937 B1 | 9/2002 | Mercereau et al. |
| 6,450,939 B1 | 9/2002 | Grimm |
| 6,471,632 B1 | 10/2002 | Jahrmarkt et al. |
| 6,482,143 B1 | 11/2002 | Slater et al. |
| 6,497,646 B1 * | 12/2002 | Candelaria et al. ............ 600/7 |
| 6,497,647 B1 | 12/2002 | Tucker |
| 6,554,760 B2 | 4/2003 | Lamoureux et al. |
| 6,572,525 B1 | 6/2003 | Yoshizumi |
| 6,709,381 B2 | 3/2004 | Munro, III |
| 2002/0049411 A1 | 4/2002 | Lamoureux et al. |
| 2002/0058057 A1 | 5/2002 | Kaplan |
| 2002/0169354 A1 | 11/2002 | Munro, III |

(Continued)

Primary Examiner—John P. Lacyk
(74) Attorney, Agent, or Firm—Stroock & Stroock & Lavan LLP

(57) ABSTRACT

An apparatus in one example comprises a first spacer component that serves to separate a plurality of implantation seeds. The first spacer component comprises an end portion that is configured to receive and hold any one of: a first one of the plurality of implantation seeds; and a second spacer component. The second spacer component comprises an end portion that is configured to receive and hold any one of: a second one of the plurality of implantation seeds; and a third spacer component.

25 Claims, 1 Drawing Sheet

U.S. PATENT DOCUMENTS

| | | |
|---|---|---|
| 2002/0177748 A1 | 11/2002 | Munro, III |
| 2003/0084988 A1 | 5/2003 | Terwilliger et al. |
| 2003/0088140 A1 | 5/2003 | Terwilliger et al. |
| 2003/0088141 A1 | 5/2003 | Terwilliger et al. |
| 2003/0088142 A1 | 5/2003 | Terwilliger et al. |
| 2003/0088144 A1 | 5/2003 | Terwilliger et al. |
| 2003/0092958 A1 | 5/2003 | Terwilliger et al. |
| 2003/0171637 A1 | 9/2003 | Terwilliger et al. |
| 2004/0054249 A1 | 3/2004 | Visscher et al. |

* cited by examiner

END PORTION OF FIRST IMPLANTATION SEED SPACER THAT RECEIVES AND HOLDS ANY ONE OF IMPLANTATION SEED AND SECOND IMPLANTATION SEED SPACER

TECHNICAL FIELD

The invention relates generally to implantation seeds and more particularly to spacing of implantation seeds.

BACKGROUND

Bodily cancers are commonly treated using radiation therapy. Radiation therapy employs high energy radiation to kill cancer cells. One type of radiation therapy is brachytherapy, in which a source of radiation is in direct contact with an afflicted tissue. A common brachytherapy treatment, transperineal seed implantation, involves placing radioactive seeds in the prostate gland to kill prostate gland cancer cells. A physician employs tools such as ultrasound, computerized axial tomography ("CAT") scans, and X-ray images in concert with dose-planning computer software programs to evaluate the medical condition of a patient. The physician constructs an optimal treatment plan to evenly distribute radiation throughout the afflicted tissue. Radioactive seeds of discrete radioactive strengths are inserted through multiple implantation needles at positions in the prostate gland corresponding to the treatment plan. Multiple implantation needles are required to insert the radioactive seeds into multiple locations in the afflicted tissue, with each needle containing a specified arrangement of the radioactive seeds. Non-radioactive spacers between the radioactive seeds are used to achieve a desired placement of the radioactive seeds specified by the physician's treatment plan.

The implantation needles are accurately located in the prostate gland utilizing a grid template and ultrasound visualization of the implantation needles once they are inserted into the prostate gland. The eventual position of the radioactive seeds and spacers (if utilized) is inferred from the position of the carrier implant needle prior to withdrawal. This procedure is detailed in an article entitled "Ultrasound Guided Transperineal Implantation for the Treatment of Early Stage Prostate Cancer" by Grimm, Blasko, and Ragde, in *The Atlas of The UrologicalClinics of North America*, Vol. II, No. 2, October 1994. In 2000, roughly 35% of all men diagnosed with localized prostate gland cancer were treated with radioactive seed implants compared with only about 4% in 1995. Radioactive seed implants have gained widespread acceptance due to the many patient benefits, including long-term results comparable with alternative therapies such as radical prostatectomy and external beam radiation therapy without the degree of impotence and incontinence seen following treatment.

In the radioactive seed implant technique, exact positioning of the radioactive seeds is critical to ensuring that the radiation dose delivered to the prostate gland matches the radiation dose prescribed in the physician's treatment plan. As one shortcoming, the radioactive seed implant technique does not prevent the movement of the radioactive seeds in the prostate gland once the implantation needle is removed. Radioactive seeds can migrate within the prostate gland after implantation, and can even move outside the confinement of the prostate gland. As another shortcoming, the initial radioactive seed positioning can be influenced by the technique used to withdraw the implantation needle, whereby the radioactive seeds and spacers are drawn along the implantation needle track as the implantation needle is removed from the prostate gland.

Horowitz (U.S. Pat. No. 4,815,449) describes a radioactive seed delivery system comprising an elongated member made of bioabsorbable material with radioactive seeds dispersed within the elongated member. The elongated member is essentially non-deflecting and is designed for direct insertion into the prostate gland. As one shortcoming, the radioactive seed delivery system does not allow for a variable positioning of the radioactive seeds. As another shortcoming, the radioactive seed delivery system is expensive to realize due to the cost of the process of encapsulating the radioactive seeds within the elongated member.

Grimm (U.S. Pat. Nos. 6,010,446 and 6,450,939) describes spacer elements manufactured from a bioabsorbable material comprising a center section and two cup-like end sections. The cup-like end sections serve to directly hold and receive adjacent radioactive seeds. A series of radioactive seeds and spacer elements form an integral unit which would maintain the relative position of the radioactive seeds in the prostate gland. The spacer elements ensure radioactive seed location following implantation. As one shortcoming, the spacer elements do not easily allow for a variable distance of separation between adjacent radioactive seeds without manufacturing and distributing different size spacer elements for every possible radioactive seed spacing required by a treatment plan.

Thus, a need exists for enhanced spacer elements to separate and hold seeds.

SUMMARY

The invention in one embodiment encompasses an apparatus. The apparatus includes a first spacer component that serves to separate a plurality of implantation seeds. The first spacer component comprises an end portion that is configured to receive and hold any one of: a first one of the plurality of implantation seeds; and a second spacer component. The second spacer component comprises an end portion that is configured to receive and hold any one of: a second one of the plurality of implantation seeds; and a third spacer component.

Another embodiment of the invention encompasses an apparatus. The apparatus includes a plurality of substantially similar spacer components made of a material absorbable in living tissue. The plurality of substantially similar spacer components are linkable to create a variable sized separator. The variable sized separator is useable to maintain a separation between a first radioactive seed and a second radioactive seed.

Yet another embodiment of the invention encompasses a method. A plurality of substantially similar spacer components are linked together to separate a first seed from a second seed. The first seed is coupled to a first end portion of a first spacer component of the plurality of substantially similar spacer components. A second end portion of the first spacer component is coupled to a first end portion of a second spacer component of the plurality of substantially similar spacer components. The second seed is coupled to a final spacer component of the plurality of substantially similar spacer components.

DESCRIPTION OF THE DRAWINGS

Features of exemplary implementations of the invention will become apparent from the description, the claims, and the accompanying drawings in which:

DETAILED DESCRIPTION

Figure 1:
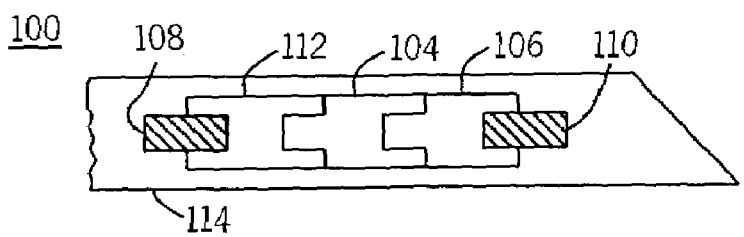
FIG. 1 is a representation of one exemplary implementation of an apparatus that comprises a spacer component that serves to separate a plurality of implantation seeds.
Figure 2:
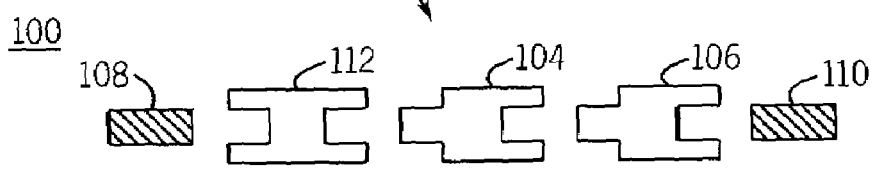
FIG. 2 is one exploded representation of the spacer component and the plurality of implantation seeds of the apparatus of FIG. 1.

Turning to FIGS. 1 and 2, an apparatus 100 in one example comprises a plurality of components such as a first spacer component that serves to separate a plurality of implantation seeds. The first spacer component comprises an end portion that is configured to receive and hold any one of a first one of the plurality of implantation seeds, and a second spacer component. The second spacer component comprises an end portion that is configured to receive and hold any one of a second one of the plurality of implantation seeds, and a third spacer component. A number of such components can be combined or divided in the apparatus 100.

In one example, the apparatus 100 comprises a string 102 of one or more spacer components 104 and 106 and one or more seeds 108 and 110. An attachment component 112 may couple one of the one or more spacer components 104 and 106 to one of the one or more seeds 108 and 110.

The seeds 108 and 110 comprise implantation seeds. The seeds 108 and 110, in one example, comprise radioactive implantation seeds. The seeds 108 and 110 deliver a radiation dose to a tissue, for example, afflicted tissue. In one application, the seeds 108 and 110 deliver a radiation dose to cancer afflicted tissue within a prostate gland. A brachytherapy treatment plan uses the string 102 to administer the radiation dose in accordance with a treatment plan prepared by a physician for a patient. The treatment plan represents the desired distribution pattern for the seeds 108 and 110 in the afflicted tissue. The physician employs medical tools such as ultrasound imaging, computerized axial tomography ("CAT") scans, and X-ray imaging in concert with dose-planning computer software programs for evaluating the medical condition of the patient. Each patient's afflicted tissue varies in size, shape, and location. The present stage of cancer in the afflicted tissue may also vary. Based on the multiple variables of the afflicted tissue and the treatment plan, the physician determines a desired distance of separation for the seeds 108 and 110. The spacer components 104 and 106 allow for a flexibility when constructing the string 102 by allowing for variable spacing. Also, linking the spacer components 104 and 106 to generate the variable spacing replaces a need to use different sized spacing elements. The spacer components 104 and 106 comprise a substantially similar design. The spacer components 104 and 106 are linkable to create a variable sized separator. The variable sized separator is useable to maintain a separation between the seeds 108 and 110.

The string 102 of the one or more spacer components 104 and 106 and the one or more seeds 108 and 110 serves to establish and maintain a distance of separation between the seeds 108 and 110. The distance of separation is based on a number of the spacer components 104 and 106 located between the seeds 108 and 110. The string 102 may contain any number and combination of seeds 108 and 110 and spacer components 104 and 106. The distance of separation may be increased by placing an additional spacer component substantially similar to the spacer components 104 and 106 between the seeds 108 and 110. The distance of separation may be decreased by removing one or more of the spacer components 104 and 106 from between the seeds 108 and 110. The distance of separation is defined by the physician's treatment plan and the strand 102 is constructed to achieve the distance of separation. The string 102, in one example, comprises a complete string of the one or more spacer components 104 and 106 and the one or more seeds 108 and 110. The string 102, in another example, comprises a portion of a complete string of the one or more spacer components 104 and 106, the one or more seeds 108 and 110, and additional spacer components and seeds.

To deliver the radiation dose to the afflicted tissue the physician loads the string 102 into an implant needle 114. In one example, the implant needle 114 comprises an eighteen gage implant needle. In another example, the implant needle 114 comprises another implant needle used by the physician. The physician injects the string 102 from the implant needle 114 into the afflicted tissue in a desired pattern. The seeds 108 and 110 are held in place in the afflicted tissue by the spacer components 104 and 106. The spacer components 104 and 106 prevent the seeds 108 and 110 from migrating within the afflicted tissue or out of the afflicted tissue.

The attachment component 112, in one example, serves to couple a first seed of the seeds 108 and 110 with a second seed of the seeds 108 and 110. The attachment component 112, in another example, serves to couple a first spacer component of the spacer components 104 and 106 with a second spacer component of the spacer components 104 and 106. The attachment component 112, in yet another example, serves to couple a seed of the seeds 108 and 110 with a spacer component of the spacer components 104 and 106.

Figure 3:
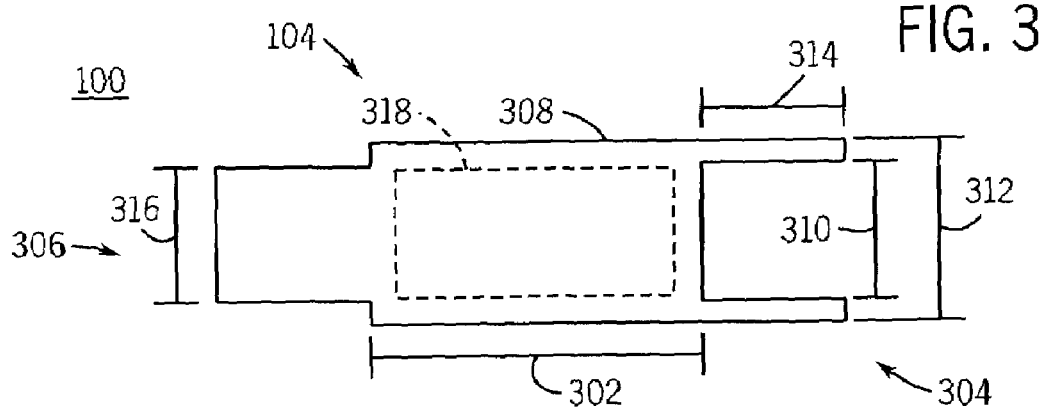
FIG. 3 is a representation of one exemplary configuration of the spacer component of the apparatus of FIG. 1.

Turning to FIGS. 1 and 3, the spacer component 104 serves to illustrate one embodiment of the one or more spacer components 104 and 106. The spacer component 104 provides a distance of separation corresponding to dimension 302 to the seeds 108 and 110. The spacer component 104 comprises a cylindrical shape. A largest diameter of the spacer component 104 is small enough to enable the spacer component 104 to pass through the implant needle 114, for example, the eighteen gage implant needle. The spacer component 104 comprises end portions 304 and 306 and a center portion 308.

The spacer component 104 comprises a material that is absorbable in living tissue, for example, bioabsorbable polymers such as polylactide, glycolide, caprolactone, polydioxanone, poly (trimethylene carbonate), and copolymers of the above listed bioabsorbable polymers. Based on the rigidity of the bioabsorbable polymer of the spacer component 104, the spacer component 104 may be rigid or flexible. Different bioabsorbable polymers may be used to make the spacer component 104 more or less flexible. Structural modifications to the spacer component 104, for example, a hollow body within the spacer component 104 may make the spacer component 104 more or less flexible.

The end portion 304 of the spacer component 104 receives and holds any one of the seeds 108 and 110, and the spacer component 106. The end portion 304 comprises a cup-like configuration. For example, the end portion 304 comprises an inner diameter 310, an outer diameter 312, and a dimension 314.

The inner diameter 310 of the end portion 304 is substantially similar to or slightly larger than a diameter of the seeds 108 and 110, and a mating diameter of the spacer component 106. Therefore, the inner diameter 310 may receive and hold any one of the seeds 108 and 110, and the spacer component 106. The inner diameter 310 typically corresponds to the diameter of one of the seeds 108 and 110, for example, about 0.8 millimeters. Therefore, the inner diameter 310 is able to receive and hold the seeds 108 and 110. However, the inner diameter 310 may be sized to allow the end portion 304 to receive and hold any size seed. The size of the inner diameter 310 is relative to a strength of the attachment between the spacer component 104 and any one of the seeds 108 and 110, and the spacer component 106. For a tighter fit and a stronger attachment, the inner dimension 310 may be reduced. For a looser fit and a weaker attachment, the inner dimension 310 may be increased.

The outer diameter 312 of the end portion 304 is small enough to enable the end portion 304 to pass through the implant needle 114. In one example where the implant needle 114 comprises the eighteen gage implant needle, the outer diameter 312 would typically be about one millimeter to allow the spacer component 104 to pass through the eighteen gage implant needle. However, the outer diameter 312 may be sized to allow the spacer component 104 to pass through any size implant needle.

The dimension 314 of the end portion 304 corresponds to a depth of the cup-like configuration. The dimension 314 may be between 0.1 and 0.2 centimeters. However, different values of the dimension 314 will achieve different levels of strength in the attachment between the spacer component 104 and any one of the seeds 108 and 110, and the spacer component 106. Alternatively, the end portion 304 comprises a flared receptacle to facilitate connection with any one of the seeds 108 and 110, and the spacer component 106. The end portion 304 may be otherwise altered to facilitate holding any one of the seeds 108 and 110, and the spacer component 106.

The end portion 306 of the spacer component 104 fits into the cup-like configuration of the end portion 304 of an adjacent spacer component, for example, spacer component 106. The end portion 306 of the spacer component 104 also fits into a cup-like configuration of an adjacent attachment component, for example, attachment component 112. The end portion 306 comprises a diameter 316 substantially similar to or slightly smaller than the inner diameter 310 of the end portion 304, for example, 0.8 millimeters. The diameter 316 is also substantially similar to or slightly smaller than an inner diameter of the cup-like configuration of the attachment component 112. Therefore, upon an engagement of the end portion 306 of the spacer component 104 with the cup-like configuration of the spacer component 106 or the attachment component 112, the cup-like configuration of the spacer component 106 or the attachment component 112 receives and holds the end portion 306 of the spacer component 104. The engagement, in one example, comprises a snug fit between the end portion 306 of the spacer component 104 and the cup-like configuration of the spacer component 106 or the attachment component 112.

The center portion 308 of the spacer component 104 provides the distance of separation corresponding to the dimension 302. In one example, the distance of separation that corresponds to the dimension 302 is between 0.5 and 1.0 centimeters. In another example, the distance of separation corresponding to the dimension 302 is any desired value to adapt to the requirements of the treatment plan. In one example, the center portion 308 comprises a solid bioabsorbable material. In another example, the center portion 308 comprises a cavity 318 encapsulated within the bioabsorbable material. The cavity 318 may comprise one or more individual cavities or may pass completely through the spacer component 104. The cavity 318 promotes detection of the spacer component 104 by an imaging component, for example, ultrasound imaging, computerized axial tomography scans, and X-ray imaging. A portion of the cavity 318 may contain contrast agents to additionally promote detection of the spacer component 104 by the imaging component, for example, one or more of ultrasound contrast agents, gadolinium, gadolinium salts, X-ray markers, air pockets, electronic sensors, and microchips. The contrast agents enhance the visibility of the spacer component 104 by the imaging component during implantation. The contrast agents also enhance the visibility of the spacer component 104 to promote location of the spacer component 104 after implantation.

Figure 4:
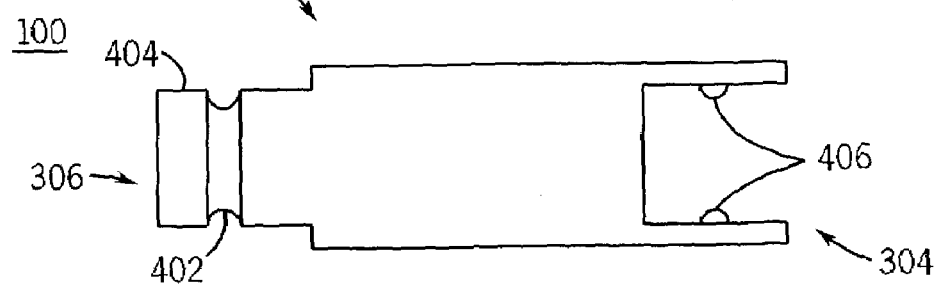
FIG. 4 is a representation of another exemplary configuration of the spacer component of the apparatus of FIG. 1.

Turning to FIGS. 1 and 4, the spacer component 104 serves to illustrate another embodiment of the one or more spacer components 104 and 106. The spacer component 104 of FIG. 4 is analogous to the spacer component 104 of FIG. 3 with the addition of a groove 402 to promote an increase of a holding effect between the end portion 306 of the spacer component 104 and the end portion 304 of the spacer component 106 or the attachment component 112. In one example, the groove 402 comprises a latitudinal groove in an outer surface 404 of the end portion 306. The groove 402 provides a supplemental gripping feature to the end portion 306 when inserted into the end portion 304 of the spacer component 106 or the attachment component 112. The end portion 304 may additionally comprise a rib 406 within the cup configuration that engages with the groove 402 upon engagement of the end portion 306 of the spacer component 104 with the end portion 304 of the spacer component 106. The groove 402 serves to promote detection of the spacer component 104 by an imaging component, for example, ultrasound imaging, computerized axial tomography scans, and X-ray imaging.

The end portion 304 and/or the end portion 306 comprises an indicator mark to differentiate between the end portion 304 and the end portion 306. In one example, the indicator mark comprises the groove 402 that provides an indication that differentiates the end portion 306 from the end portion 304 to an observer. In another example, one of the end portion 304 and the end portion 306 is colored with an ink or a dye that provides the indication that differentiates the end portion 306 from the end portion 304 to the observer. In yet another example, one of the end portion 304 and the end portion 306 comprises a visible mechanical alteration, such as, making the one of the end portion 304 and the end portion 306 pointed or roughening a surface of the one of the end portion 304 and the end portion 306. The indication that differentiates the end portion 306 from the end portion 304 allows for ease of assembly, as the indication clearly illustrates a proper head to toe arrangement of the spacer components 104 and 106 and seeds 108 and 110. Additional or alternative positional indicators or gripping features, for example, longitudinal striations or barbs could be used in place of the groove 402.

The steps or operations described herein are just exemplary. There may be many variations to these steps or operations without departing from the spirit of the invention. For instance, the steps may be performed in a differing order, or steps may be added, deleted, or modified.

Although exemplary implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. A brachytherapy apparatus, comprising:
an assembled string of a plurality of implantation seeds including at least one first spacer, and at least one second spacer, the first spacer having two ends and cavities at each end, the cavities sized to partly receive and form a coupled connection with a seed, the second spacer having first and second ends, with a cavity formed in the first end extending from the first end towards the middle of the spacer, the cavity sized to form a coupled connection with an end of an implantation seed, said seed being partly received in said cavity, with portions of the seed not received in the cavity, the second end having a linking projection sized to be received in and form a coupled connection with the cavity of a first or second spacer, and a gripping structure is formed on the linking projection, the structure being sized and arranged to promote an increase in a gripping effect between the cavity portion of the first spacer component and the linking projection of the second spacer component.

2. The brachytherapy apparatus of claim 1, wherein the cavity portions of the first and second spacer components are substantially similar.

3. The brachytherapy apparatus of claim 1, wherein the cavity portions of the respective first and second spacer components comprise cup configurations, wherein the projection portions of the second spacer components comprise a mating relationship with the cup configurations of the respective first spacer components.

4. The brachytherapy apparatus of claim 3, wherein the cavity portion of the first or second spacer component comprises a rib within the cup configuration, wherein the projection portion of the second spacer component comprises a groove;
wherein the rib comprises a mating relationship with the groove.

5. The brachytherapy apparatus of claim 1, wherein the projection of a second spacer is received in and coupled with the cavity of another second, the end portion of the first spacer component comprises a first end portion, wherein the first spacer component further comprises a second end portion;
wherein one of the first end portion and the second end portion comprises an indicator to differentiate between the first end portion and the second end portion.

6. The brachytherapy apparatus of claim 1, wherein the second spacer component further comprises a center portion that comprises a dimension that contributes to a distance of separation between the plurality of implantation seeds.

7. The brachytherapy apparatus of claim 6, wherein the center portion comprises a structure that serves to promote detection of the first spacer component by an imaging component.

8. The brachytherapy apparatus of claim 7, wherein a portion of the structure is filled with a contrast agent, wherein the contrast agent promotes additional detection of the first spacer component by the imaging component.

9. The brachytherapy apparatus of claim 1, wherein the plurality of implantation seeds comprises a first implantation seed and a second implantation seed, wherein the first implantation seed and the second implantation seed are separated by a predetermined distance;
wherein based on the predetermined distance one or more additional spacer components separate the first implantation seed from the second implantation seed;
wherein the one or more additional spacer components comprise respective end portions that are configured to receive and hold any one of:
a third one of the plurality of implantation seeds; and
a first one of the one or more additional spacer components that comprises an end portion that is configured to receive and hold any one of:
a fourth one of the plurality of implantation seeds; and
a second one of the one or more additional spacer components.

10. The brachytherapy apparatus of claim 1,
wherein the plurality of implantation seeds comprises a first implantation seed and a second implantation seed, wherein the first implantation seed and the second implantation seed are separated by a predetermined distance;
wherein the first spacer receives and holds the first implantation seed in one cavity thereof, wherein the other cavity portion of the first spacer couples with one or more additional spacer components based on the predetermined distance;
wherein the one or more additional spacer components comprise respective end portions that are configured to receive and hold any one of:
a third one of the plurality of implantation seeds; and
a first one of the one or more additional spacer components that comprises an end portion that is configured to receive and hold any one of:
a fourth one of the plurality of implantation seeds; and
a second one of the one or more additional spacer components;
wherein one of the one or more additional spacer components is coupled with the second implantation seed.

11. The brachytherapy apparatus of claim 1, wherein the cavity portion of the second spacer comprises an inner diameter and an outer diameter, wherein the second end portion comprises an outer diameter;
wherein the outer diameter of the second end portion comprises a substantially similar to slightly smaller diameter compared to the inner diameter of the first end portion.

12. The brachytherapy apparatus of claim 1, wherein the first spacer component comprises a cylindrical shape, wherein a largest diameter of the first spacer component is small enough to enable the first spacer component to pass through an implant needle.

13. The brachytherapy apparatus of claim 1, wherein the largest diameter of the second spacer component is small enough to pass through an eighteen gage implant needle.

14. The brachytherapy apparatus of claim 1, wherein the second spacer component comprises a material that is absorbable by living tissue.

15. The brachytherapy apparatus of claim 1, wherein the first spacer component and the second spacer component serves to separate a plurality of radioactive seeds.

16. The brachytherapy apparatus of claim 15, wherein the first spacer component and second spacer component and the plurality of radioactive seeds are implanted into a prostate, wherein the first spacer component serves to maintain a desired separation between the plurality of radioactive seeds in the prostate, wherein the plurality of radioactive seeds serve to treat prostate cancer.

17. The brachytherapy apparatus of claim 1, wherein the first spacer component, and the second spacer component, are interchangeable.

18. A brachytherapy apparatus, comprising:

a plurality of substantially similar spacer components made of a material absorbable in living tissue, wherein the plurality of substantially similar spacer components are linkable to create a variable sized separator;

wherein the variable sized separator is useable to maintain a separation between a first radioactive seed and a second radioactive seed, wherein the plurality of substantially similar spacer components comprise a first spacer component comprising an end portion having a cavity that is linkable with an end portion of the second spacer component and a second spacer component comprising a linking projection and a gripping structure is formed on the linking projection, the structure being sized and arranged to promote an increase in a gripping effect between the cavity portion of the first spacer component and the linking projection of the second spacer component.

19. The brachytherapy apparatus of claim 18, wherein the end portion of the first spacer component comprises a recess, wherein the end portion of the second spacer component couples with the recess of the first spacer component.

20. The brachytherapy apparatus of claim 18, wherein the variable sized separator comprises any number of the plurality of substantially similar spacer components needed to achieve a predetermined separation distance between the first radioactive seed and the second radioactive seed, wherein the predetermined separation distance is based on a patient specific radiation treatment plan.

21. A method of linking a plurality of substantially similar spacer components together to separate a first seed from a second seed comprising the steps of:

coupling the first seed to a first end portion of a first spacer component of the plurality of substantially similar spacer components;

coupling a second end portion of the first spacer component to a first end portion of a second spacer component of the plurality of substantially similar spacer components;

coupling the second seed to a final spacer component of the plurality of substantially similar spacer components; and promoting an increase of a gripping effect between the first and second spacer components through employment of a gripping structure on the second end portion of the first spacer component.

22. The method of claim 21, wherein the first and second seeds comprise first and second radioactive seeds and further comprising the step of:

implanting the plurality of substantially similar spacer components and the first and second radioactive seeds into a portion of tissue.

23. The method of claim 22, wherein the step of implanting the plurality of substantially similar spacer components and the first and second radioactive seeds into the portion of tissue comprises the step of:

employing the plurality of substantially similar spacer components to hold the first and second radioactive seeds in a predetermined location within the portion of tissue.

24. The method of claim 21, wherein the step of linking the plurality of substantially similar spacer components together to separate the first seed from the second seed comprises the steps of:

selecting the first spacer component to comprise the first end portion that is configured to receive and hold any one of:

the first seed; and an additional spacer component of the plurality of substantially similar spacer components.

25. The brachytherapy apparatus of claim 1, wherein the coupled connection of the projection of the end portion of the second spacer and the cavity portion of the first spacer is such that the first and second spacers abut one another without a gap therebetween at the circumferences thereof.

* * * * *